United States Patent [19]

Levenson et al.

[11] Patent Number: 4,914,210
[45] Date of Patent: Apr. 3, 1990

[54] OLIGONUCLEOTIDE FUNCTIONALIZING REAGENTS

[75] Inventors: Corey Levenson, Oakland; Chu-An Chang, El Cerrito, both of Calif.; Fred T. Oakes, Rochester, N.Y.

[73] Assignee: Cetus Corporation, Emeryville, Calif.

[21] Appl. No.: 104,200

[22] Filed: Oct. 2, 1987

[51] Int. Cl.[4] ............................. C07F 9/24; C07F 9/65
[52] U.S. Cl. ..................... 548/413; 558/168; 558/169; 558/171; 536/27; 552/104
[58] Field of Search .................. 558/168, 169, 171; 260/389; 548/413

[56] References Cited

U.S. PATENT DOCUMENTS 4,522,735  6/1985  Chasar ................................. 252/49.9
4,582,789  4/1986  Sheldon, III et al. ................ 435/6
4,617,261  10/1986  Sheldon, III et al. ............... 435/6

OTHER PUBLICATIONS

Greene, "Protective Groups in Organic Synthesis", pp. 34, 35, 72, 73, 201, 265.
Chem. Abst. 107(3):23650d.
Mitsunobu, Jan. 1981, Synthesis, pp. 1–28.

Primary Examiner—Anton H. Sutto
Attorney, Agent, or Firm—Kevin R. Kaster; Albert P. Halluin

[57] ABSTRACT

Oligonucleotide functionalizing reagents are disclosed which are useful in introducing sulfhydryl, amino and additional hydroxyl groups into oligonucleotides. The reagents are substantially linear in structure, at one end provided with a phosphoramidite moiety, at an opposing end provided with a sulfhydryl, amino or hydroxyl moiety, the two ends linked through a hydrophilic spacer chain. Methods of using and synthesizing the novel reagents are disclosed as well.

7 Claims, No Drawings

OLIGONUCLEOTIDE FUNCTIONALIZING REAGENTS

BACKGROUND OF THE INVENTION

1. Technical Field

The present invention relates generally to oligonucleotide functionalizing reagents, and more particularly relates to novel reagents for the introduction of sulfhydryl, amino and hydroxyl groups into synthetic oligonucleotides.

2. Description of the Prior Art

Non-isotopically labeled synthetic DNA fragments have found broad application in molecular biology—e.g., in the areas of DNA sequencing, DNA probe-based diagnostics, and the like. The reagents disclosed herein facilitate the labeling of oligonucleotides with specific groups by incorporating one or more unique, modifiable sulfhydryl, amino or hydroxyl groups within the oligonucleotide at any position, typically at the 5' terminus.

Several references teach methods of introducing a sulfhydryl or an amino group at the 5' terminus of synthetic oligonucleotides. For example, Connolly, in *Nuc. Acids Res.* 13(12): 4485–4502 (1985) and in *Nuc. Acids Res.* 15(7): 3131–3139 (1987), describes a method of incorporating a sulfhydryl moiety into synthetic DNA using S-trityl-O-methoxy-morpholinophosphite derivatives of 2-mercaptoethanol, 3-mercaptopropan-1-ol and 6-mercaptohexan-1-ol—i.e., reagents given by the formula

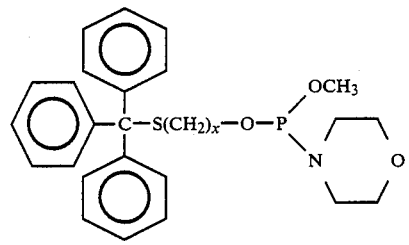

(1)

where x is 2, 3 or 6. Connolly further describes derivatization of the sulfhydryl-containing oligonucleotides with thiol-specific probes.

Coull et al., in *Tetrahedron Lett.* 27(34): 3991–3994 (1986), describe a reaction which incorporates an aliphatic primary amino group at the 5' terminus of oligonucleotides using an N-protected aliphatic amino phosphoramidite given by the structure

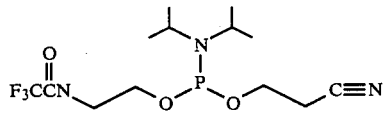

(2)

as the functionalizing reagent; Sproat et al., *Nuc. Acids Res.* 15(15): 6181–6196 (1987), describes a similar method. Smith et al., in *Nuc. Acids Res.* 13(7): 2399–2411 (1985), also describes a method for synthesizing oligonucleotides containing a 5' aliphatic amino group, by direct reaction of oligonucleotides with protected phosphoramidite derivatives of 5'-amino-5'-deoxythymidine. An additional functionalizing reagent for introducing primary amines at the 5' terminus is that sold under the trademark "Aminolink" by Applied Biosystems, Inc., and given by the formula

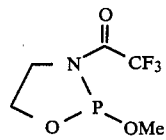

(3)

This reagent requires treatment with the activating agent dimethylaminopyridine prior to use and also necessitates deprotection with thiophenol, a sensitive, malodorous reagent.

These and other prior art methods suffer from one or more of the following disadvantages:

(1) A short spacer chain linking the 5' terminus of the oligonucleotide to the sulfhydryl, amino or hydroxyl group results in destabilization of the derivatived structure—i.e., proximity of a solid support or a bulky labeling species to the oligonucleotide chain causes steric interference and thus hinders use of the derivatived oligonucleotide in probe-based applications;

(2) A hydrophobic spacer chain linking the 5' terminus of the oligonucleotide to the sulfhydryl, amino or hydroxyl group provides problems with solubility in the aqueous solvents commonly used in DNA probe-based methods;

(3) Conventionally used functionalizing reagents are often incompatible with commonly used DNA synthesis methodology, primarily because the functionalizing reagents are incompatible with the reagents and solvents typically used therewith;

(4) Conventionally used functionalizing reagents are frequently difficult to synthesize in high yield, necessitating complex, multi-step reactions;

(5) As noted above in the case of Aminolink, certain known reagents require treatment with multiple activating agents immediately prior to use;

(6) Conventionally used functionalizing reagents do not allow for "tacking on" of multiple spacer chains to increase the distance between the terminal sulfhydryl, amino or hydroxyl moiety and the oligonucleotide chains, nor, generally, do they allow for multiple functionalization along an oligonucleotide chain;

(7) Conventionally used functionalizing reagents do not generally allow for functionalization at positions other than at the 5' hydroxyl terminus; and (8) Conventionally used functionalizing reagents sometimes require deprotection under harsh conditions, in such a way that, frequently, the deprotection reaction is not readily monitorable.

There is thus a need in the art for oligonucleotide functionalizing reagents which address the aforementioned considerations.

SUMMARY OF THE INVENTION

It is accordingly a primary object of the present invention to provide oligonucleotide functionalizing reagents which overcome the above-mentioned disadvantages of the prior art.

In particular, it is an object of the present invention to provide oligonucleotide functionalizing reagents which give stable, water-soluble derivatized oligonucleotides upon coupling.

It is another object of the invention to provide oligonucleotide functionalizing reagents which allow for multiple functionalization at the 5' terminus of an oligonucleotide chain—i.e., enable sequential addition of linked spacer chains.

It is a still further object of the invention to provide oligonucleotide functionalizing reagents which may be used in conjunction with standard DNA synthesis reagents and protocols.

It is yet a further object of the invention to provide oligonucleotide functionalizing reagents which may be synthesized via a straightforward procedure in high yield.

It is another object of the invention to provide oligonucleotide functionalizing reagents which require treatment only with standard activating agents prior to use, and which may be coupled to an oligonucleotide chain in such a way that the coupling reaction is easily monitored by spectroscopic means.

It is still another object of the invention to provide a method of functionalizing oligonucleotide chains using the aforementioned oligonucleotide functionalizing reagents to introduce one or more sulfhydryl, amino or hydroxyl moieties into oligonucleotide chains, typically at the 5' terminus.

It is yet another object of the invention to provide a method of derivatizing oligonucleotide chains with detectable species bound to the chains through a sulfhydryl, amino or hydroxyl group.

It is a final object of the invention to provide methods of synthesizing the aforementioned oligonucleotide functionalizing reagents.

Additional objects, advantages and novel features of the invention will be set forth in part in the description which follows, and in part will become apparent to those skilled in the art on examination of the following, or may be learned by practice of the invention. The objects and advantages of the invention may be realized and attained by means of the instrumentalities and combinations particularly pointed out in the appended claims.

In one aspect of the invention, oligonucleotide functionalizing reagents are provided which are substantially linear in structure, at one end provided with a phosphoramidite moiety which is reactive with hydroxyl groups on an oligonucleotide chain, at an opposing end provided with a sulfhydryl, amino or hydroxyl group, the two ends linked by a relatively long hydrophilic chain. In a preferred embodiment, the hydrophilic chain is a polyether spacer having at least about 8 carbon atoms therein. Preferred specific structures will be outlined below.

In another aspect of the invention, these reagents are used to functionalize an oligonucleotide chain to introduce, after deprotection, at least one sulfhydryl, amino or hydroxyl group. The coupling reaction is effected using standard techniques for coupling a phosphoramidite to the terminal hydroxyl group of an oligonucleotide. After functionalization, the oligonucleotide may be derivatized at the introduced sulfhydryl, amino or hydroxyl moiety with a detectable species.

Various novel synthetic routes to the functionalizing reagents will be described below. Each of these routes is quite straightforward, minimizing the number of synthetic steps involved, and allowing recovery of the product in high yield.

DETAILED DESCRIPTION OF THE INVENTION

1. Definitions

"Functionalizing" as used herein means incorporating a protected or unprotected sulfhydryl (-SH) or amino (-NHα where α is hydrogen or lower alkyl) moiety into an oligonucleotide chain. The sulfhydryl, amino or hydroxyl group introduced by functionalization is typically spaced apart from the oligonucleotide chain by a spacer chain as will be described herein. "Oligonucleotide functionalizing reagents" are thus reagents which effect the incorporation of sulfhydryl, amino or hydroxyl groups into oligonucleotide chains, yielding "functionalized oligonucleotide chains".

"Derivatizing" as used herein means reacting a functionalized oligonucleotide at the added sulfhydryl, amino or hydroxyl moiety with a detectable species, i.e., one that serves as a label in probe-based applications. A "derivatized" oligonucleotide is thus one that is detectable by virtue of the "derivatizing" species.

An "oligonucleotide" as used herein is a single-stranded or double-stranded, typically a single-stranded, chain of nucleotide, typically deoxyribonucleotide, monomer units. While the reagents and methods of the present invention may be used in conjunction with a single nucleotide monomer or with a full-length DNA strand, the "oligonucleotides" herein are typically single-stranded and of from about 2 to about 400 monomer units, and more typically, for most probe-based applications, from about 2 to about 100 monomer units.

Use of the derivatized oligonucleotides in "probe-based" applications is intended to mean use of the labeled chain to detect or quantify oligonucleotide segments or sequences in a specimen.

A sulfhydryl or amino group that is "protected" is one that has been reacted with a protecting moiety such that the resulting protected group will not be susceptible to any sort of chemical reaction during the synthetic step or steps during which the protecting group is present.

By "stability" of the functionalized or derivatized oligonucleotide chain is meant substantial absence of steric interference as well as chemical stability under the conditions of most probe-based applications.

By "lower alkyl" and "lower alkoxy" are meant alkyl and alkoxy substituents, respectively, having from about 1 to 6, more typically from about 1 to 3, carbon atoms.

Where aromatic substituents are indicated, it is to be understood that each individual aromatic ring may be substituted at one or more carbon atoms with moieties which do not substantially affect function or reactivity.

2. Structure of the Novel Functionalizing Reagents

As noted above, the novel compounds are substantially linear functionalizing reagents having a phosphoramidite moiety at one end linked through a hydrophilic spacer chain to an opposing end provided with a protected or unprotected sulfhydryl, amino or hydroxyl moiety. These functionalizing reagents are in general given by the structure

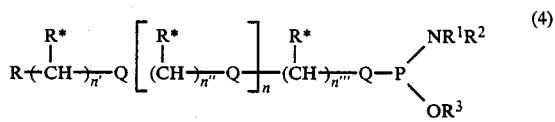

wherein:
R is a protected or unprotected amino, sulfhydryl or hydroxyl moiety;

R* is hydrogen, -CH₂OH, or a substituent having the structure

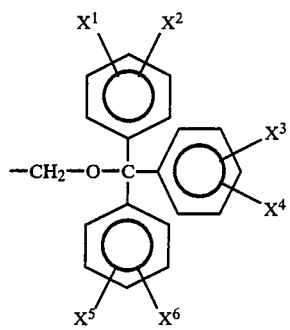
(5)

in which
X¹, X², X³, X⁴, X⁵ and X⁶ may be the same or different and are selected from the group consisting of hydrogen, lower alkyl and lower alkoxy;
R¹ and R² are independently selected from the group consisting of hydrogen and lower alkyl;
R³ is β-cyanoethyl or methyl;
the Q moieties are selected from the group consisting of

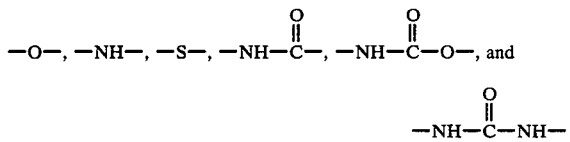

and may be the same or different;
n', n" and n''' are integers in the range of 2 and 10 inclusive, more typically in the range of 2 and 6 inclusive; and
n is an integer which may be larger than 30, but typically is in the range of 2 and 30 inclusive, and more typically is in the range of 2 and 20 inclusive.

Structure (6) represents one example of a particularly preferred embodiment

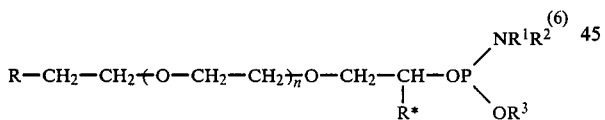
(6)

where R, R*, R¹, R², R³ and n are as given above. The hydrophilic spacer chain in such as case is a polyether linkage—e.g., as shown, formed from polyetylene glycol. (In other embodiments encompassed by general structure (4), the spacer chain may also be formed from polypropylene glycol or the like, or from poly(oxyalkyleneamines) such as the Jeffamines sold by Texaco Chemical Co.)

When it is desired to couple the functionalizing reagent to an oligonucleotide chain, at any position, generally, that a nucleoside phosphoramidite could be coupled to the chain, the R moiety is a protected sulfhydryl, amino or hydroxyl moiety. The protecting group is selected so that the sulfhydryl, amino or hydroxyl moiety remains intact during the phosphoramidite coupling step—i.e., in which the phosphoramidite group of the reagent reacts with the hydroxyl moiety on the oligonucleotide chain. The conditions for this reaction are those used in the conventional method of synthesizing DNA via the so-called "phosphoramidite" route, described, for example, in Beaucage and Caruthers, *Tetrahedron Lett.* 22: 1859–1862 (1981).

Examples of particularly preferred protecting groups where the functionalizing reagent is a sulfhydryl functionalizing reagent are given by R=

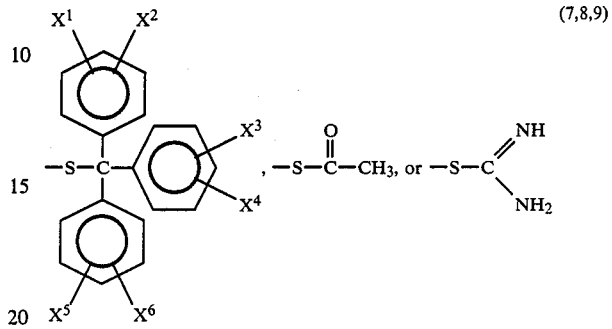
(7,8,9)

Examples of particularly preferred protecting groups where the functionalizing reagent is an amine functionalizing reagent are given by R=

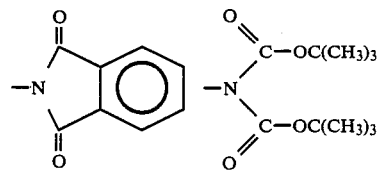
(10,11)

It is to be understood that the aforementioned exemplary protecting groups are illustrative only, and that any number of sulfhydryl and amine protecting groups may be used so long as the above-described "protecting" criteria are met.

In the case of hydroxyl functionalizing reagents, a number of hydroxyl protecting groups are available and well known to those skilled in the art. However, as R* will in most embodiments be a hydroxyl moiety protected with an acid-labile protecting group such as DMT (see structure (5)), it is preferred when R is a protected hydroxyl moiety as well that the protecting group be functionally distinguishable from that at R*, i.e., be other than acid-labile. Typical hydroxyl protecting groups for "R" are thus base-labile moieties, e.g., esters such as fluorenyl methyl chloroformate (FMOC).

The opposing end of the functionalizing reagent defined by the phosphoramidite group

(12)

is selected so as to couple to a free hydroxyl moiety, which for most uses will be the terminal 5' hydroxyl of a growing or completed oligonucleotide chain. As noted above, R¹ and R² are either hydrogen or lower alkyl, and may be the same or different; in a particularly preferred embodiment, both R¹ and R² are isopropyl. R³ is either methyl or β-cyanoethyl; in a particularly preferred embodiment, R³ is β-cyanoethyl. Use of the phosphoramidite group as a coupling means is well known in the art of DNA synthesis, and reference may be had to Beaucage and Caruthers (1981), supra, for further description on point The spacer chain

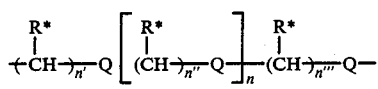   (13)

is a hydrophilic chain wherein n, n', n'' and n''' are integers having values as set forth above.

In the preferred embodiment represented by formula (6), the spacer chain is the polyether moiety

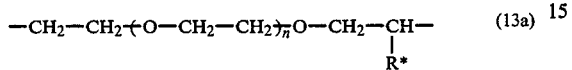   (13a)

wherein n is typically 2–30, more typically 2–20 (in some cases, however, n may be larger than 30—i.e., where increased distance is desired between the derivatizing moiety and the oligonucleotide chain).

Optimal values for n provide the spacer chain with a total of at least about 8 carbon atoms along its length. The length of the spacer chain is quite relevant to the effectiveness of the present reagents, as providing greater distance between the sulfhydryl, amino or hydroxyl group and the oligonucleotide chain: (1) facilitates coupling of the reagent to DNA; (2) avoids steric interference which would hinder hybridization and destabilize the functionalized or derivatized oligonucleotide chain; and (3) simulates a "solution" type environment in that freedom of movement of the derivatized sulfhydryl or amine moiety is enhanced. The fact that the spacer chain is hydrophilic also enhances the solubility of the functionalized or derivatized oligonucleotide chains in aqueous media.

R* is either hydrogen, -CH$_2$OH, or the aromatic substituent given by (5). Where R* is (5), it is selected so that the chromogenic cation

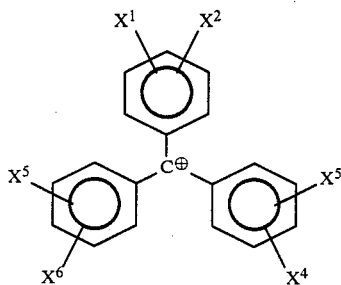   (5a)

is monitorable upon release. That is, after coupling of the functionalizing reagent to DNA, deprotection will yield cation (5a) in solution. An example of a particularly preferred substituent is dimethoxytrityl (DMT)—i.e., R* is -CH$_2$-O-DMT.

While in a preferred embodiment, as illustrated by structure (6), R* is bonded to the carbon atom adjacent to the phosphoramidite group, it is also possible that R* may be bonded to one or more other carbon atoms along the spacer chain as illustrated by formula (4).

3. Use of the Novel Reagents to Functionalize Oligonucleotide Chains

In general, the coupling reaction between the novel functionalizing reagents and a hydroxyl-containing compound may be represented by the following scheme:

(Scheme I)

X—OH + Reagent (4) $\longrightarrow$   (14)

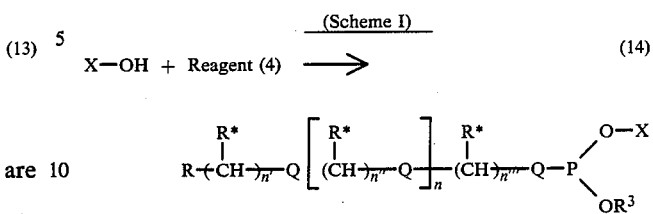

In Scheme I, X is typically an oligonucleotide chain. The reaction conditions are the same as those used in the phosphoramidite route to DNA synthesis, as noted earlier and as described, inter alia, by Beaucage and Caruthers (1981), supra.

Compound (14) is deprotected as follows. Where R* is given by formula (5), conversion to an unprotected hydroxyl group is carried out by treatment with acid. The protected amino or hydroxyl substituent at "R" is deprotected, generally, by treatment with a base. Treatment with NH$_4$OH, for example, not only deprotects the oligonucleotide chain, but, where R is amino or hydroxyl, deprotects the R substituent as well. Where R is a protected sulfhydryl moiety, deprotection may be effected with—e.g., silver nitrate.

Multiple functionalization of an oligonucleotide is possible by making use of multiple R* sites where R* is given by formula (5). After acid deprotection, further functionalization by reaction at the deprotected hydroxyl site is enabled. Thus, in the case of functionalized oligonucleotide (15), for example,

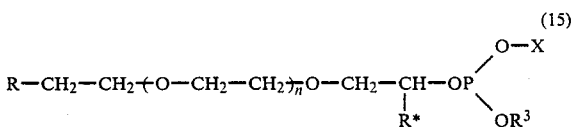   (15)

deprotection of R* and further functionalization at the -OH moiety so provided, using a standard phosphoramidite coupling procedure, gives the compound of formula (16):

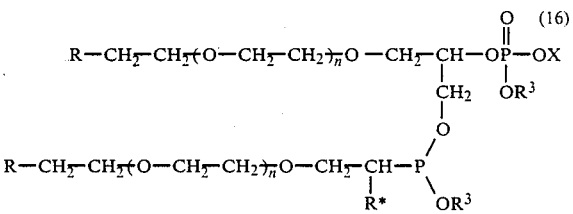   (16)

Multiple functionalization at a plurality of hydroxyl groups along an oligonucleotide chain is also possible using the same chemistry.

4. Synthesis of the Novel Reagents

The inventors herein have developed various routes to the novel reagents. For the purpose of simplicity, syntheses of the functionalizing reagents will be discussed in terms of exemplary structure (6) rather than general structure (4). It is to be understood, however, that the synthetic methods described apply, in general, substantially identically to compounds represented by (4). In a first embodiment, where the functionalizing reagent to be synthesized is an amine functionalizing reagent, Scheme II may be followed:

molar excess of the phosphoramidite is added to compound (21) in a suitable solvent, again, one that is prefer-

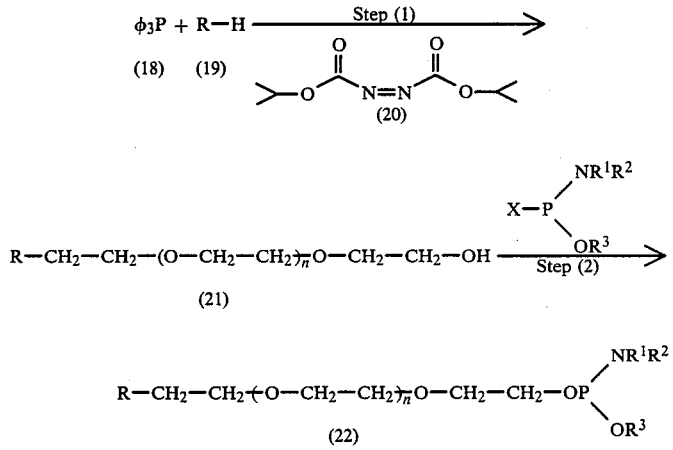

Step (1) represents the Mitsunobu reaction as is well known in the art. Briefly, the reaction involves admixture of compounds (17), (18), (19) and (20) in a polar, inorganic solvent for at least several hours, preferably overnight (see Example 1). Compound (21) is isolated and coupled to the phosphoramidite (wherein X represents a halogen, preferably chlorine) as follows. A ably a polar, organic solvent, under an inert atmosphere. Compound (22) is isolated—e.g., by column chromatography.

An alternative method of synthesizing the amine functionalizing reagents herein, and one which may also be used to give the sulfhydryl functionalizing reagents, is given by Scheme III:

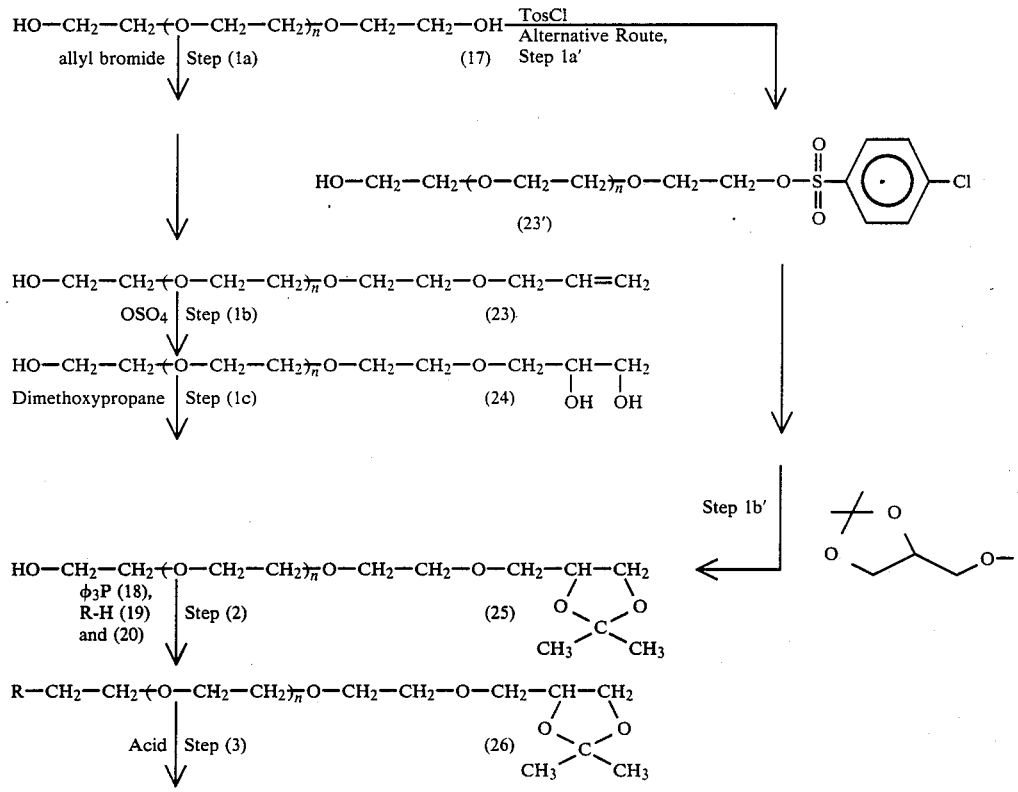

-continued
(Scheme III)

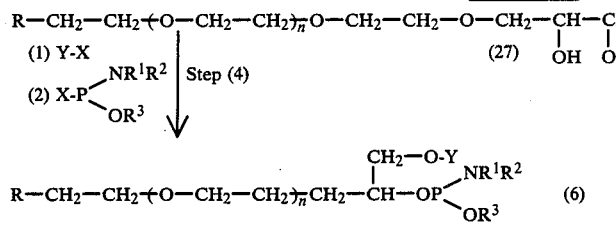

In Scheme III, steps 1a–1c and 1a'–1b' represent alternative routes to intermediate (25). In steps 1a–1c, the protected diol (25) is formed by: reaction of the polyethylene glycol (17) with allyl bromide (reaction carried out at room temperature for at least about a few hours, preferably overnight) to give (23); reaction of (23) with osmium tetroxide to give diol (24) under conventional, known conditions; and protection of the diol by reaction with 2,2-dimethoxypropane. Steps 1a'–1b' give (25) via reaction of the tosylated glycol (23') with the solketal anion. Step 2 represents the Mitsunobu reaction as shown in Scheme II, where R is as defined earlier, while the acid treatment of Step 3 deprotects the diol. Step 4-1 introduces chromogenic moiety (5a) where y is given by (5a) and Step 4-2 introduces the phosphoramidite (12). "X" in both Steps 4-1 and 4-2 is a halogen leaving group, preferably chlorine.

A third synthetic method, specific for the production of sulfhydryl functionalizing reagents, is given by Scheme IV.

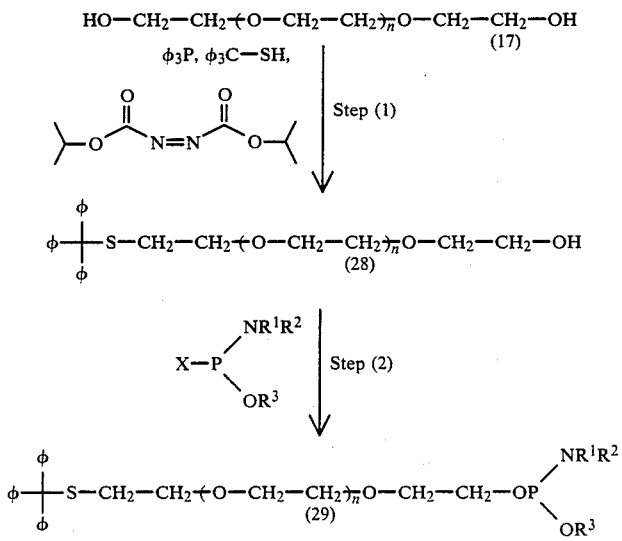

In Scheme IV, Step 1 is carried out at a low temperature, preferably about 0° C. or less, and the triphenylphosphine, diisopropylazodicarboxylate and S-tritylmercaptan are allowed to react overnight. Intermediate 28 is purified, and the phosphoramidite is added in Step 2, and (29) is obtained in good yeild. Here, "R" of structure (4) is shown as -S-C$\phi_3$ ($\phi$=phenyl throughout) but may in fact be any number of protected sulfhydryl moieties.

5. Derivatization with Labeled Species

The functionalized oligonucleotide chains prepared using the novel reagents are primarily useful in probe-based applications. That is, the primary purpose of introducing sulfhydryl, amino or additional hydroxyl groups into oligonucleotides is to enable derivatization at that site with a labeled species. The most common types of labeled species are fluorophores, chromophores, radioactive isotopes and enzymes.

Additional information on derivatization with labeled species may be found in copending application Ser. No. 103,978, filed Oct. 2, 1987, of common inventorship herewith and entitled "A Covalent Oligonucleotide-Horseradish Peroxidase Conjugate". That application, the disclosure of which is incorporated by reference herein, discloses covalent conjugates of the above-described sulfhydryl functionalizing reagents with the labeling enzyme horseradish peroxidase.

It is to be understood that while the invention has been described in conjunction with the preferred specific embodiments thereof, that the foregoing description as well as the examples which follow are intended to illustrate and not limit the scope of the invention. Other aspects, advantages and modifications within the scope of the invention will be apparent to those skilled in the art to which the invention pertains.

EXAMPLE 1

(a) Reaction of tetraethylene glycol with phthalimide (see Step(1), Scheme II): Tetraethylene glycol (38.85 g, 200 mmole) and triphenyl phosphine (52.46 g, 200 mmole) were dissolved in 200 mL of dry THF, and phthalimide (29.43 g, 200 mmole) added. A solution of diethylazo dicarboxylate (DEAD) (34.83 g; 200 mmole) in 100 mL of dry THF was added dropwise to the reaction mixture, with cooling and stirring. The reaction mixture was stirred overnight at room temperature.

Solvent was then removed under reduced pressure, and the residue partitioned between 250 mL of $H_2O$ and 250 mL of diethyl ether. The aqueous layer was washed five times with 200 mL of diethyl ether and concentrated under vacuum. The residue was dried by azeotropic distillation of toluene (3×100 mL) and weighed. The 25.89 g obtained was then purified on an $SiO_2$ column using ethyl acetate as an eluant. The product fractions were collected and concentrated to a syrup (11.75 g; 36.3 mmole; 18.2%) which was allowed to crystallize overnight.

The structure of the product obtained in (a) was confirmed by $^1H$ NMR as:

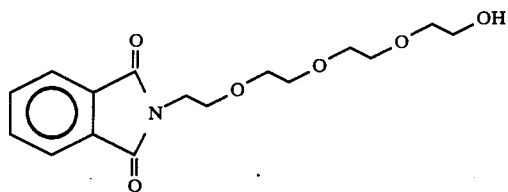

(b) Synthesis of the allyl derivative (see Step 1b, Scheme III): To a solution of the alcohol obtained in step (a) (4.67 g; 14.4 mmole) in 100 ml of dry THF was added NaH (520 mg; 21.67 mmole). The mixture was stirred for one hour, and then allyl bromide (1.9 mL; 2.61 g; 21.67 mmole) was addd. The suspension was stirred overnight, at which point it was filtered and the solvent removed under reduced pressure. The residue was purified on an $SiO_2$ column using a mixture of ethyl acetate and hexane (70:30) as eluant. Fractions containing the desired product were pooled and concentrated to a syrup weighing 2.84 g (7.82 mmole; 54.3%). Elemental analysis was as follows. Calc.: C, 62.80; H, 6.93; N, 3.85. Found: C, 62.49; H, 6.99; N, 3.82.

Proposed structure of the product obtained:

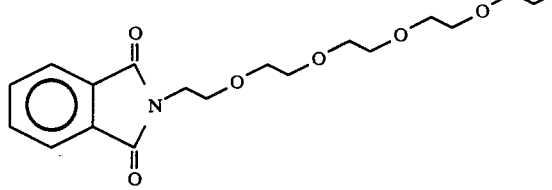

(c) Synthesis of the corresponding diol (see Step 1b, Scheme III): To a solution of the allyl ether prepared in step (b) (2.84 g: 7.82 mmole) and N-methyl morpholine N-oxide (1.83 g; 15.63 mmole) in 180 mL of $DMF/H_2O$ (8:1) was added osmium tetroxide (8.13 mL of a solution 25 mg/mL in t-butanol; 800 μmole). The resulting amber solution was stirred at room temperature. After 48 hours, a solution of sodium hydrosulfite (2.13 g) in water (10 mL) was added to the reaction mixture. A black precipitate formed and the suspension was stirred for 1 hour. The mixture was filtered and concentrated under reduced pressure. The residue was purified on an $SiO_2$ column using a mixture of methylene chloride and methanol as the eluant. Elemental analysis was as follows. Calc.: C, 62.80; H, 6.93; N, 3.85. Found: C, 62.49; H, 6.99; N, 3.82.

Proposed structure of the product

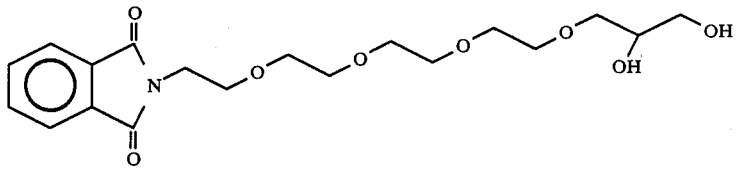

(d) Labelling with DMT: The diol obtained in part (c) (1.0 g; 2.50 mmole) was coevaporated with anhydrous pyridine (2×15 mL). The dry residue was then dissolved in 25 mL of the same. DMT-Cl (0.92 g; 2.75 mmole) was added to the solution. The reaction was carried out at room temperature and monitored by TLC ($CH_3Cl$:MeOH approximately 97:3) until appearance of the product.

After one hour, 10 mL of methanol was added and the reaction mixture was stirred for ten additional minutes. Next, the reaction was quenched with 10 mL of ice water and extracted with ethyl acetate (2×75 mL).

The organic layer was washed once with 5% $NaHCO_3$ (50 mL), twice with saturated NaCl solution and dried over $Na_2SO_4$. The product was evaporated down to an oily residue under reduced pressure.

This residue was chromatographed using the above solvent system. The final product was used without further purification in step (e). Yield: 86.3% of theoretical (1.51 g actual/1.75 g theoretical). Proposed structure of the product obtained in this step:

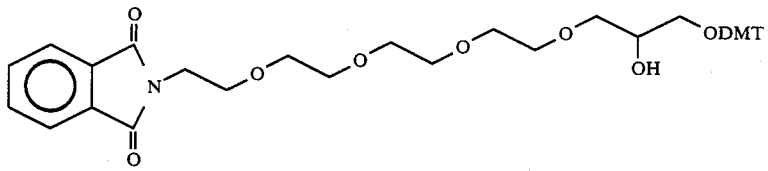

(e) Preparation of the phosphoramidite: The product obtained in step (d) (1.0 g; 1.4 mmole) was dissolved in 10 mL of acid-free chloroform and placed in a 250 mL round bottom flask preflushed with dry argon. To this solution (0.72 g, 5.6 mmole) of $[(CH_3)_2-CH]_2-N-Et$ was added. Then, the phosphoramidite

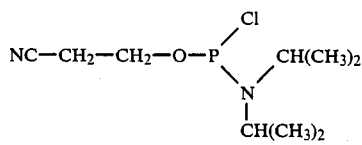

(0.66 g; 2.8 mmole) was added with a syringe over a two-minute period. The reaction was carried out at room temperature and under argon. After one hour, the mixture was transferred with 50 mL of ethyl acetate in a 250 mL separatory funnel and extracted with saturated NaCl solution four times. The organic layer was dried over $Na_2SO_4$ and evaporated down to an oily residue under vacuum. This residue was chromatographed with 1% $Et_3N$ in ethyl acetate. Yield: 48.4% of theoretical (0.610 g actual/1.26 g theoretical).

EXAMPLE 2

Essentially the same procedure was followed as set forth in Example 1, but the tetraethylene glycol starting material was not in this case initially reacted with phthalimide.

(a) Synthesis of the allyl derivative of pentaethylene glycol: To a solution of pentaethylene glycol (5.65 g; 20 mmole) in 100 mL of dry THF was added the potassium salt of t-butanol (2.24 g; 20 mmole). The mixture was stirred for 30 minutes and 18-crown-6 (53 mg; 0.2 mmole) was added. The mixture was stirred for an additional 30 minutes and then allyl bromide (2.42 g; 1.73 mL; 20 mmole) ws added. A white precipitate, presumably potassium bromide, was noted to form and stirring was continued overnight. The reaction mixture was filtered through a Whatman GFB filter, adsorbed onto 8 g of $SiO_2$, and fractionated on an $SiO_2$ column using a mixture of methylene chloride and acetone (1:1) as eluant. The pooled fractions yielded 4.28 g (13.28 mmole; 66.4%) product. Elemental analysis was as follows. Calc.: C, 55.88; H, 9.38. Found: C, 55.56; H, 9.76.

Proposed structure of the product:

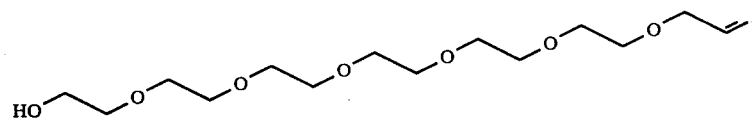

(b) Synthesis of the corresponding diol: To a solution of the allyl ether prepared in step (a) (4.28 g; 13.28 mmole) in 270 mL of a mixture of acetone and water (8:1) was added N-methyl morpholine (3.11 g; 4.6 mL; 26.55 mmole; 2 eq.) followed by osmium tetroxide (25 mg/mL in t-butanol; 338 mg; 13.5 mL; 1.33 mmole [0.1 eq.]). The reaction mixture was stirred overnight. The next morning, a solution of sodium hydrosulfite (3.62 g) in 15 mL water was added. After 45 minutes of stirring, the suspension was filtered through a Whatman GFB filter. The solvent was evaporated, the residue taken up in methanol, and the suspension filtered. The filtrate was concentrated to an amber syrup, which was then purified on $SiO_2$ using a mixture of methylene chloride, methanol, and acetic acid (80:20:5) as eluant. The fractions containing product were pooled and concentrated to yield 3.3 g (9.26 mmole; 69.7% yield) product.

Proposed structure of the product:

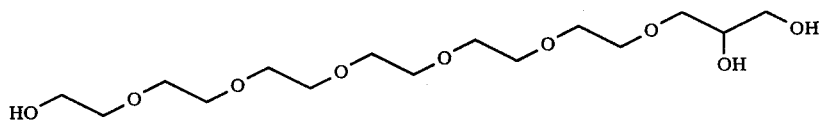

(c) The triol prepared in step (b) (3.3 g; 9.26 mmole) was taken up in 60 mL acetone and cupric sulfate (45 g; 28.20 mmole) was added. To the resulting bluish suspension was added 60 mL $H_2SO_4$, at which point the solution turned yellow. The flask was stoppered and stirred over a weekend. The suspension was then filtered through a Whatman GFB filter and the filtrate treated in 2.5 g $Ca(OH)_2$ for one hour. The suspension was filtered again and the filtrate concentrated and purified on an $SiO_2$ column. The column was run in 97:3 chloroform:methanol and then again using 8:1 chloroform:methanol. The column fractions were pooled, yielding 3.03 g (7.64 mmole; 82.5%) product.

Proposed structure of the product:

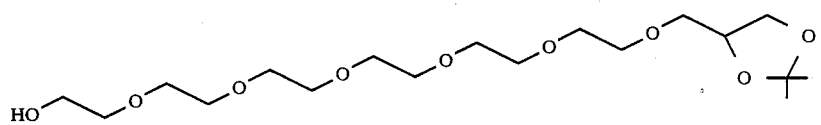

EXAMPLE 3

Synthesis of

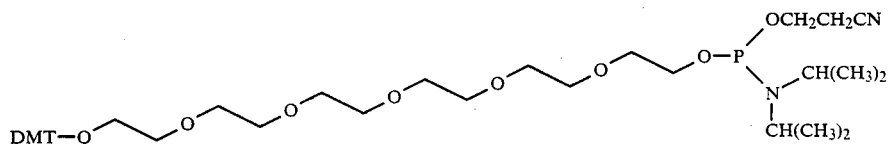

was carried out as follows.

(a) Hexaethylene glycol (10.0 g; 35.40 mmole) was coevaporated with anhydrous pyridine (3×25 mL) and then dissolved in 100 mL of the same. DMT-Cl (13.17 g; 38.94 mmole) was added to the solution. The reaction was carried out at room temperature and monitored by TLC ($CHCl_3$:MeOH approximtely 8:1) until the appearance of product. After two hours, 25 mL of methanol was added and the reaction mixture was stirred for 15 additional minutes. Next, the reaction was quenched with 50 mL ice water and extracted with ethyl acetate (3×150 mL). The organic layer was washed with 5% NaHCO₃ (2×100 mL), saturated NaCl (2×100 mL), dried over Na₂SO₄ and then evaporated down to an oily residue (yellowish color). This oily residue was chromatographed on a silica gel column (400 g). The column was eluted first with CHCl₃:MeOH (approximately 97:3), then with CHCl₃:MeOH (approximately 90:10). The fractions were combined and evaporated to dryness to give an oily residue. The material obtained was presumed to be of the structure

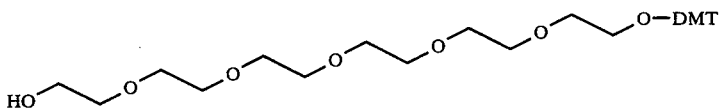

and was used without further purification in the synthesis of the corresponding phosphoramidite.

(b) The procedure of Example 1(e) was followed using 2.0 g (3.40 mmole) of the compound obtained in (a), 1.6 g (6.80 mmole) of the phosphoramidite

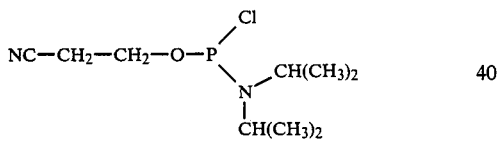

and 1.76 g (13.60 mmole) of [(CH₃)₂-CH]-N-Et. Elemental analysis of the product was as expected for C₄₂H₆₁N₂O₁₀P×H₂O. Calc.: C, 63.49; H, 7.93; N, 3.52. Found: C, 63.36; H, 7.95; N, 4.11. Yield: 85.4% of theoretical (2.28 g/2.67 g).

EXAMPLE 4

(a) Synthesis of

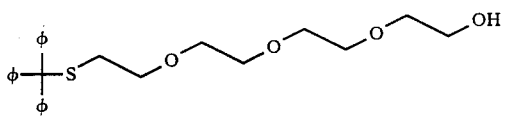

(compound (26); see Step 1, Scheme IV) was carried out as follows. To a 0° C. solution of triphenylphosphine (7.87 g; 30 mmole) in 75 mL dry THF was added the azodicarboxylate(NCOOCH(CH₃))₂ (6.07 g; 30 mmole) with stirring. After one hour, a solution of tetraethylene glycol (5.83 g; 30 mmole) in 10 mL dry THF was added. All material dissolved to give a pale yellow solution. After one hour, a solution of the mercaptan φ₃C-SH in 20 mL dry THF was added dropwise with cooling and stirring. The reaction mixture was stirred overnight and the solvent removed under reduced pressure. The residue was applied to an SiO₂ column and fractionated using methylene chloride followed by a mixture of mixture of methylene chloride and CH₃CN (2:1). The material was rechromatographed on SiO₂ using CH₃CN as eluant, and the product was removed from φ₃P=O by taking small (approximately 15 mL) fractions. The fractions were pooled, yielding 5.22 g (11.53 mmole; 38.4% overall; 77% of theoretical). Elemental analysis was as follows. Calc.: C, 71.65; H, 7.12; S, 7.08. Found: C, 71.32; H, 7.21; S, 7.15.

(b) Synthesis of the corresponding phosphoramidite

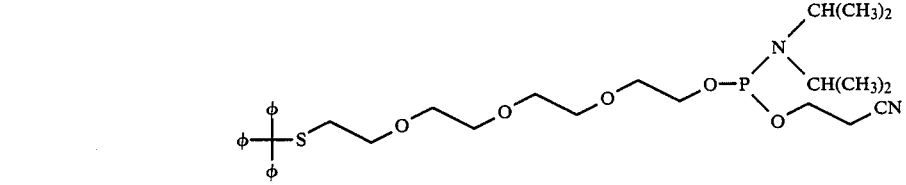

was then carried out according to the method described in Example 1(e), using the reaction product of step (a) (4.22 g; 9.30 mmole), the phosphoramidite

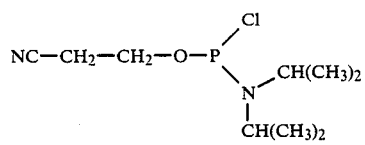

(4.40 g; 18.60 mmole) and [(CH₃)₂-CH]₂-N-Et (4.81 g; 37.20 mmole). Yield: 75.3% of theoretical (4.57 g/6.07 g).

We claim:
1. An oligonucleotide functionalizing reagent having the structure:

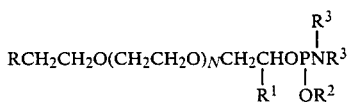

wherein
R is a protected amino, sulfhydryl, or hydroxyl moiety;
R¹ is a protected hydroxymethyl or hydrogen;
R² is methyl or β-cyanoethyl,
R³ is lower alkyl; and
N is an integer in the range of 2 through 20 inclusive.
2. The compound of claim 1, wherein R is a protected amino moiety.
3. The compound of claim 1, wherein R is a protected sulfhydryl moiety.
4. The compound of claim 1, wherein R is a protected hydroxyl moiety.
5. The compound of claim 2 that is

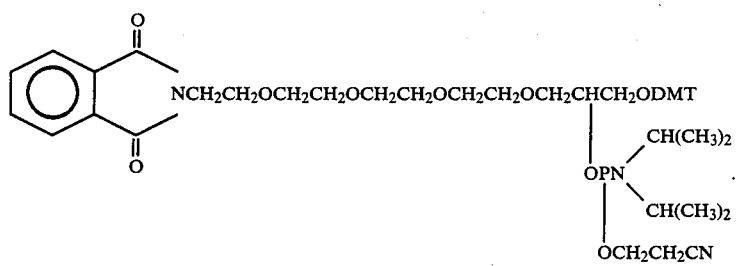
6. The compound of claim 3 that is
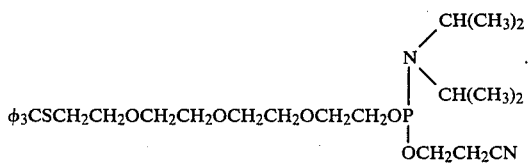
7. The compound of claim 4 that is
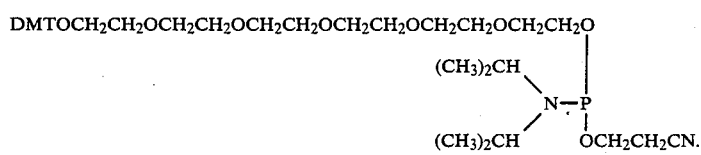
* * * * *